(12) United States Patent
Gupta et al.

(10) Patent No.: US 8,895,065 B2
(45) Date of Patent: *Nov. 25, 2014

(54) SINGLE UNIT ORAL DOSE PHARMACEUTICAL COMPOSITION COMPRISING LEVODOPA, CARBIDOPA AND ENTACAPONE OR SALTS THEREOF

(75) Inventors: Yatendra Kumar Gupta, Aurangabad (IN); Girish Kumar Jain, Delhi (IN); Munish Talwar, Panchkula (IN); Manoj Mashalkar, Latur (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,258

(22) Filed: May 29, 2012

(65) Prior Publication Data

US 2012/0231051 A1 Sep. 13, 2012

Related U.S. Application Data

(63) Continuation of application No. 13/060,180, filed as application No. PCT/IB2009/053699 on Aug. 22, 2009.

(30) Foreign Application Priority Data

Aug. 22, 2008 (IN) .................... IN2008/MUM/1779

(51) Int. Cl.
| | | |
|---|---|---|
| *A61K 31/195* | (2006.01) | |
| *A61K 9/24* | (2006.01) | |
| *A61K 9/00* | (2006.01) | |
| *A61K 45/06* | (2006.01) | |
| *A61K 9/20* | (2006.01) | |
| *A61K 31/198* | (2006.01) | |
| *A61K 31/277* | (2006.01) | |

(52) U.S. Cl.
CPC .............. *A61K 45/06* (2013.01); *A61K 9/2059* (2013.01); *A61K 9/209* (2013.01); *A61K 31/198* (2013.01); *A61K 31/277* (2013.01)
USPC ........... 424/472; 424/400; 424/457; 424/464; 424/465; 424/468; 424/488; 514/565

(58) Field of Classification Search
None
See application file for complete search history.

(56) References Cited

U.S. PATENT DOCUMENTS

| | | |
|---|---|---|
| 6,500,867 B1 | 12/2002 | Virkki et al. |
| 2004/0166159 A1* | 8/2004 | Han et al. ...................... 424/468 |
| 2008/0118556 A1 | 5/2008 | Devane et al. |

FOREIGN PATENT DOCUMENTS

| | | |
|---|---|---|
| WO | WO2007073702 A2 | 7/2007 |
| WO | WO2008053297 A2 | 5/2008 |
| WO | WO 2008053297 A2 * | 5/2008 |
| WO | WO2009098661 A1 | 9/2009 |

OTHER PUBLICATIONS

Piccini (Piccini et al., The catechol-O-methyltransferase (COMT) inhibitor entacapone enhances the pharmokinetic and clinical response to Sinemet CT in Parkinson's disease, J. Neurol. Neurosurg. Psychiatry, 68 (2000) 589-594).*

Ahtila (Ahtila et al., Effect of Entacapone, a COMT Inhibitor, on the Pharmacokinetics and Metabolism of Levodopa After Administration of Controlled-Release Levodopa-Carbidopa in Volunteers, Clin. Neuropharm. 18 (1995) 46-57).*

Rinne (Rinne, et al., Entacapone enhances the response to levodopa in parkinsonian patients with motor fluctuations Neurology, 51 (1998) 1309-1314).*

* cited by examiner

*Primary Examiner* — Rachael E Bredefeld
*Assistant Examiner* — Dominic Lazaro
(74) *Attorney, Agent, or Firm* — Bio Intellectual Property Services LLC (Bio IPS); O. (Sam) Zaghmout

(57) ABSTRACT

There is provided a single unit oral dose pharmaceutical composition comprising a) levodopa or salts thereof from about 50 mg to about 300 mg in extended release form, b) carbidopa or salts thereof from about 10 mg to about 100 mg in extended release and c) entacapone or salts thereof from about 100 mg to about 1000 mg in immediate release form, optionally with other pharmaceutically acceptable excipients. The invention also relates to process of preparation of such compositions.

8 Claims, No Drawings

SINGLE UNIT ORAL DOSE PHARMACEUTICAL COMPOSITION COMPRISING LEVODOPA, CARBIDOPA AND ENTACAPONE OR SALTS THEREOF

CROSS-REFERENCE TO RELATED APPLICATIONS

This application is a Continuation of U.S. application Ser. No. 13/060,180, filed Jun. 6, 2011, now pending, which entered the National Phase of Serial No. PCT/IB2009/053699; filed Aug. 22, 2009 which claims priority to Application No. IN2008MU0001779, filed Aug. 22, 2008. The entire disclosure of these prior applications are hereby incorporated by reference.

FIELD OF THE INVENTION

There is provided a single unit oral dose pharmaceutical composition comprising a) levodopa or salts thereof from about 50 mg to about 300 mg in extended release form, b) carbidopa or salts thereof from about 10 mg to about 100 mg in extended release and c) entacapone or salts thereof from about 100 mg to about 1000 mg in immediate release form, optionally with other pharmaceutically acceptable excipients. The invention also relates to process of preparation of such compositions.

BACKGROUND OF THE INVENTION

Entacapone, an inhibitor of catechol-O-methyltransferase (COMT), used in the treatment of Parkinson's disease as an adjunct to levodopa/carbidopa therapy.

The chemical name of entacapone is (E)-2-cyano-3-(3,4-dihydroxy-5-nitrophenyl)-N,N-diethyl-2-propenamide. Its empirical formula is $C_{14}H_{15}N_3O_5$, and its structural formula is:

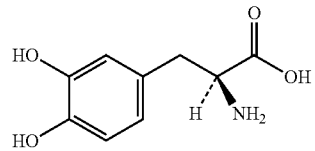

Carbidopa, an inhibitor of aromatic amino acid decarboxylation, is a white, crystalline compound, slightly soluble in water. It is designated chemically as (−)-L-(α-hydrazino-(α-methyl-β-(3,4-dihydroxybenzene) propanoic acid. Its empirical formula is $C_{10}H_{14}N_2O_4$ and its structural formula is:

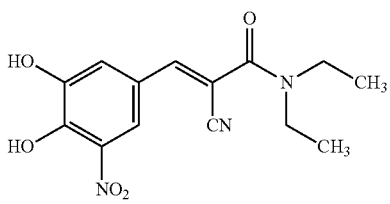 [SMILES: CCN(CC)C(=O)/C(C#N)=C/c1cc(O)c(O)c([N+](=O)[O-])c1]

Levodopa, an aromatic amino acid, is a white, crystalline compound, slightly soluble in water. It is designated chemically as (−)-L-α-amino-β-(3,4-dihydroxybenzene)propanoic acid. Its empirical formula is $C_9H_{11}NO_4$, and its structural formula is:

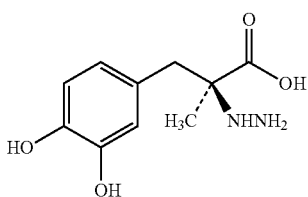 [SMILES: C[C@@](Cc1ccc(O)c(O)c1)(NN)C(=O)O]

U.S. Pat. Nos. 6,500,867 and 6,797,732 disclose oral solid tablet compositions comprising entacapone, levodopa and carbidopa, or pharmaceutically acceptable salts or hydrates thereof, and a pharmaceutically acceptable excipient.

U.S. Pat. No. 7,094,427 and US 20040166159 disclose a composition comprising immediate release and extended release component.

US 20080051459 discloses a method of treating Parkinson's disease comprising administering pharmaceutically effective amount of a composition comprising levodopa.

US 20070275060 disclose an extended release tablet comprising an extended release composition comprising levodopa; and an immediate or rapid release composition comprising carbidopa.

WO 07/073702 discloses a multi-layered tablet providing three different release profiles.

US 20060173074 disclose a method for the treatment of restless legs syndrome in a mammal.

Entacapone is available as immediate release composition under the trade name Comtan®. The marketed strength is 200 mg.

The triple combination of levodopa, carbidopa and entacapone is available as immediate release composition in different strengths. For example Stalevo® 50 (containing 12.5 mg of carbidopa, 50 mg of levodopa and 200 mg of entacapone), Stalevo® 75 (containing 18.75 mg of carbidopa, 75 mg of levodopa and 200 mg of entacapone), Stalevo®100 (containing 25 mg of carbidopa, 100 mg of levodopa and 200 mg of entacapone), Stalevo®125 (31.2575 mg of carbidopa, 125 mg of levodopa and 200 mg of entacapone), Stalevo®150 (containing 37.5 mg of carbidopa, 150 mg of levodopa and 200 mg of entacapone) and Stalevo®200 (containing 50 mg of carbidopa, 200 mg of levodopa and 200 mg of entacapone).

Parkinson's disease is a slowly progressive disease, in which the symptoms get worse over time. Therefore, the symptoms will change and evolve. The pattern of symptoms can vary for each person. Over a number of years, however, some people may see changes in the way their medication controls their symptoms. These changes are commonly known as motor fluctuations. Over time, symptoms begin to come back before it is time to take next dose of levodopa medication. This change in symptoms is called "wearing-off." As "wearing-off" becomes more noticeable, the amount of time for a good response to levodopa (known as "on" time) shortens and the time for poor response to levodopa (known as "off" time) may lengthen.

In the early stages of the disease, the brain is able to store enough dopamine. This permits smoother release of dopamine in the brain. It also provides a more constant control of symptoms. However, as Parkinson's disease gets worse, the brain has fewer cells that can take up levodopa and store it as dopamine for release when levels are low. Because of this reduced ability to store dopamine in the brain, symptoms may return after shorter periods of time (e.g. "wearing-off"). If someone with a reduced ability to store dopamine is given too much levodopa, it may lead to side effects (e.g. dyskinesia).

It may be possible to better control these symptoms by changing or adjusting the treatment. As these motor fluctuations emerge, other unwanted side effects may occur. These include involuntary movements, known as dyskinesia (e.g. twisting/turning movements) or dystonia (e.g. prolonged muscle cramping). The patients treated for Parkinson's disease may frequently develop motor fluctuations characterized by end-of-dose failure, peak dose dyskinesia and akinesia, with levodopa therapy ("wearing off") in which the patient suffers from unpredictable swings from mobility to immobility. More than 50% of patients with Parkinson's disease develop motor response fluctuations (the "wearing off" phenomenon) after treatment with levodopa therapy. Symptoms of wearing off include bradykinesia, dystonia, tremors, decreased manual dexterity, paresthesia, muscle pain, voice softness.

It is believed that the 'wearing off' effect can be minimized in patients with a treatment regimen, which provides less rapid dissolution properties and providing a more even plasma level profile of levodopa. When administered in conjunction with levodopa, entacapone increases the bioavailability of levodopa by facilitating its passage across the blood-brain barrier. Hence, entacapone is approved as an adjunct to levodopa therapy in Parkinson's disease. However, the dosage of currently available formulation of carbidopa, levodopa and entacapone i.e. Stalevo® is given eight times a day. The frequent dosing of these formulations is associated with more fluctuating plasma entacapone concentrations. Further, this regimen is not patient compliant.

Further, it has been observed that it is very inconvenient for the patient to take a tablet of Sinemet CR and Comtan simultaneously number of times a day, which leads to patient non-compliance especially in Parkinson's patient. Further, literature also suggests when the three ingredients are present together vis a vis entacapone, carbidopa and levodopa, it leads to decrease in bioavailability of entacapone and levodopa. Therefore, the marketed formulation Stalevo contains substantial portion of carbidopa separate from levodopa and carbidopa. Additionally, literature also reports destabilization of triple combination formulation in presence of microcrystalline cellulose.

Hence, there is a need for patient compliant entacapone composition and/or triple combination comprising levodopa, carbidopa and entacapone that will dissolve slowly and provide a more even plasma level profile in patients with entacapone or levodopa/entacapone/carbidopa treatment regimen.

SUMMARY OF THE INVENTION

In one aspect of the invention, there is provided a single unit oral dose pharmaceutical composition comprising a) levodopa or salts thereof from about 50 mg to about 300 mg in extended release form, b) carbidopa or salts thereof from about 10 mg to about 100 mg in extended release and c) entacapone or salts thereof from about 100 mg to about 1000 mg in immediate release form, optionally with other pharmaceutically acceptable excipients.

In another aspect of the invention, there is provided a method of treating Parkinson's disease in a mammal, comprising administering to a mammal in need thereof, a single unit oral dose pharmaceutical composition comprising a) levodopa or salts thereof from about 50 mg to about 300 mg in extended release form, b) carbidopa or salts thereof from about 10 mg to about 100 mg in extended release and c) entacapone or salts thereof from about 100 mg to about 1000 mg in immediate release form, optionally with other pharmaceutically acceptable excipients.

In another aspect of the invention, there is provided a method of reducing the "wearing off" phenomena in Parkinson's patients, comprising administering to patient in need thereof, a single unit oral dose pharmaceutical composition comprising a) levodopa or salts thereof from about 50 mg to about 300 mg in extended release form, b) carbidopa or salts thereof from about 10 mg to about 100 mg in extended release and c) entacapone or salts thereof from about 100 mg to about 1000 mg in immediate release form, optionally with other pharmaceutically acceptable excipients.

In another aspect, there is provided a process for preparing a single unit oral dose pharmaceutical composition comprising a) levodopa or salts thereof from about 50 mg to about 300 mg in extended release form, b) carbidopa or salts thereof from about 10 mg to about 100 mg in extended release and c) entacapone or salts thereof from about 100 mg to about 1000 mg in immediate release form, wherein the said process comprises of: a) coating or mixing levodopa, carbidopa with pharmaceutically acceptable rate controlling polymers; b) entacapone with one or more pharmaceutically acceptable excipients; c) mixing the blend of step a) and b) and converting it into suitable dosage form.

Embodiments of the pharmaceutical composition may include one or more of the following features. For example, the pharmaceutically acceptable excipients may include one or more of fillers, binders, lubricants, sweeteners, coloring and flavoring agents, glidants, disintegrants, and the like.

The details of one or more embodiments of the inventions are set forth in the description below. Other features, objects and advantages of the inventions will be apparent from the description and claims.

DETAILED DESCRIPTION OF THE INVENTION

The inventors while working on the levodopa, entacapone, and carbidopa compositions have noticed that when levodopa or carbidopa is formulated in extended release form, it allows for the continuous release of levodopa or carbidopa over a prolonged period. Extended release composition maintains extended release of levodopa and carbidopa thereby leading to non-fluctuating constant plasma levels of levodopa and carbidopa. This further leads to reduction in the "wearing-off" phenomena, which is observed in Parkinson's patients due to fluctuating plasma levels.

The inventors have further unexpectedly found that Sinemet CR and Comtan can be combined together in a single unit oral dose fixed combination without effecting bioavailability of any one active in presence of other. Even microcrystalline cellulose can also be used in the fixed dose combination without having any destabilizing effect on fixed dose composition. This fixed dose combination further leads to increase in patient compliance.

The term 'extended release' as used herein refers to specific release of drug over a specified time period, which may extend from 4 hr to 24 hrs or more.

The extended release in the pharmaceutical composition may be achieved by one or more of coating or embedding in matrix using with hydrophilic or hydrophobic polymers or by attachment to ion-exchange resins. Further, extended release may be achieved by osmotic oral release technology also.

One tablet of the said composition exhibits no significant difference in rate and/or extent of absorption of entacapone as compared to 2-4 tablets of 200 mg of immediate release entacapone commercially marketed as Comtan® and levodopa and carbidopa as compared to one tablet of Sinemet® CR administered at the interval of 3-4 hours.

"Bioequivalency" is established by a 90% Confidence Interval (CI) of between 0.80 and 1.25 for both $C_{max}$ and AUC under USFDA regulatory guidelines, or a 90% CI for AUC of between 0.80 to 1.25 and a 90% CI for $C_{max}$ of between 0.70 to 1.43 under the European EMEA regulatory guidelines.

The term "confidence interval" as used herein refers to plain meaning known to ordinary skill in the art. Confidence interval refers to a statistical range with a specified probability that a given parameter lies within the range.

The term "covariance" as used herein refers to plain meaning known to ordinary skill in the art. It is a statistical measure of the variance of two random variables that are observed or measured in the same mean time period. This measure is equal to the product of the deviations of corresponding values of the two variables from their respective means.

The extended release pharmaceutical composition may include one or more of tablet, bilayered tablet, trilayered tablet, tablet in tablet, capsule, powder, disc, caplet, granules, pellets, granules in capsule, minitablets, minitablets in capsule, pellets in capsule, sachet and the like.

Levodopa, carbidopa or entacapone may be present in the form of powder, granules, pellets, beads, microtablets, minitablets and crystals.

The amount of entacapone in these pharmaceutical compositions varies from about 100 mg to about 1000 mg. The amount of levodopa in these pharmaceutical compositions varies from about 50 mg to about 300 mg. The amount of carbidopa in these pharmaceutical compositions varies from about 10 to about 100 mg.

Suitable rate controlling hydrophilic or hydrophobic polymers comprise one or more of polyvinyl acetate, cellulose acetate, cellulose acetate butyrate, cellulose acetate propionate, ethyl cellulose, a fatty acid, a fatty acid ester, an alkyl alcohol, a wax, shellac, rosin, zein (prolamine from corn), povidone, kollidon SR, a poly(meth)acrylate, microcrystalline cellulose or poly(ethylene oxide), polyuronic acid salts, cellulose ethers, xanthan gum, tragacanth gum, gum karaya, guar gum, acacia, gellan gum locust bean gum, alkali metal salts of alginic acid or pectic acid, sodium alginate, potassium alginate, ammonium alginate, hydroxypropyl cellulose, hydroxy ethyl cellulose, hydroxypropyl methyl cellulose, carboxyvinyl polymers, polymerized gelatin, shellac, methacrylic acid copolymer type C NF, cellulose butyrate phthalate, cellulose hydrogen phthalate, cellulose propionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethyl cellulose (CMEC), hydroxypropyl methylcellulose acetate succinate (HPMCAS), and acrylic acid polymers and copolymers like methyl acrylate, ethyl acrylate, methyl methacrylate and/or ethyl methacrylate with copolymers of acrylic and methacrylic acid esters (Eudragit NE, Eudragit RL, Eudragit RS) and the like. Polymer may be used from 0.1-50% by weight of the composition.

The extended release pharmaceutical composition may comprise one or more pharmaceutically acceptable excipients. The pharmaceutically acceptable excipients may include diluents, binders, disintegrants, surfactants, lubricants, glidants and the like.

Suitable binder may one or more of, povidone, starch, stearic acid, gums, hydroxypropylmethyl cellulose and the like. Binder may be used from 0.1% to 40% by weight of the composition Suitable diluent may be one or more of, microcrystalline cellulose, mannitol, calcium phosphate, calcium sulfate, kaolin, dry starch, powdered sugar and the like. Diluent may be used from 1 to 50% by weight of the composition.

Suitable disintegrant may be one or more of starch, croscarmellose sodium, crospovidone, sodium starch glycolate and the like. Disintegrant may be used from 2-20% by weight of the composition.

Suitable lubricant may be one or more of magnesium stearate, zinc stearate, calcium stearate, stearic acid, sodium stearyl fumarate, hydrogenated vegetable oil, glyceryl behenate and the like. Lubricant may be used from 0.1-5% by weight of the composition.

Suitable glidant may be one or more of colloidal silicon dioxide, talc or cornstarch and the like. Glidant may be used from 0.1-5% by weight of the composition.

The pharmaceutical composition may be prepared by mixing entacapone with pharmaceutically acceptable excipients to form an entacapone blend. Levodopa and carbidopa may be mixed with one or more pharmaceutically acceptable polymers and excipients to form levodopa carbidopa blend. The entacapone blend and levodopa-carbidopa blend may be mixed with other pharmaceutically acceptable excipients and converted into suitable dosage form.

The invention is further illustrated by the following examples which are provided merely to be exemplary of the invention and do not limit the scope of the invention. Certain modifications and equivalents will be apparent to those skilled in the art and are intended to be included within the scope of the invention.

EXAMPLES

The composition of batches is provided in Table 1 to 23. Following formulations are representatives of the preferred compositions of the invention. The preparation of example is detailed below.

Example-I

TABLE 1

Pharmaceutical composition of the invention

| Ingredients | % w/w |
|---|---|
| Entacapone IR layer/Portion | |
| Entacapone | 38.41 |
| Mannitol | 6.73 |
| Sodium starch glycolate | 3.85 |
| Corn Starch | 9.42 |
| Croscarmellose sodium | 4.62 |
| Povidone | 1.51 |
| Purified water | q.s. |
| Extragranular Ingredients | |
| Magnesium stearate | 0.77 |
| Levodopa and Carbidopa CR layer/Portion | |
| Levodopa | 19.22 |
| Carbidopa | 5.19 |
| Microcrystalline Cellulose | 4.62 |
| Povidone | 3.46 |
| Purified Water | q.s. |
| Extragranular Ingredients | |
| Poly Vinyl Pyrrolidone | 1.73 |
| Magnesium Stearate | 0.38 |

Procedure:

Entacapone Layer/Portion: Entacapone and mannitol were co-milled and sifted. Cornstarch, croscarmellose sodium and sodium starch glycolate were co-sifted separately. The materials were placed in granulator and mixed. Povidone was dissolved in purified water and granulated with the mixed material. The granulated contents were dried. Magnesium stearate was sifted and mixed with the dried granules.

Levodopa and Carbidopa Layer/Portion:

Levodopa, Carbidopa and microcrystalline cellulose were co-sifted and mixed. Povidone was dissolved in Purified water and granulate with above mixed contents. The granulated contents were dried. Magnesium stearate was sifted with polyvinyl pyrrolidone and mixed with the dried granules.

Compression

Both the entacapone layer/portion and Levodopa and Carbidopa layer/portion were compressed into bilayered tablets or into tablet in tablet with entacapone surrounding the levodopa-carbidopa inlay tablet.

TABLE 2

Dissolution data of composition prepared as per example I.

| Time (hrs) | % Drug released | |
|---|---|---|
| | Levodopa | Carbidopa |
| 0.5 | 45 | 45 |
| 1 | 58 | 58 |
| 2.5 | 94 | 92 |
| 4 | 96 | 95 |

| Time (min) | % Drug released (Entacapone) |
|---|---|
| 10 | 51 |
| 20 | 70 |
| 30 | 79 |
| 45 | 85 |

Table 2 provides the dissolution data of composition prepared as per formula given in table 1. For determination of drug release rate of entacapone, USP Type 2 Apparatus (rpm 50) was used wherein 900 ml of pH 5.5 phosphate buffer at 37° C.±0.5° C. was used as medium. Further, for determination of drug release rate of levodopa and carbidopa, USP Type 2 Apparatus (rpm 50) was used wherein 900 ml of 0.1 N HCl at 37° C.±0.5° C. was used as medium.

Example-II

TABLE 3

Pharmaceutical composition of the invention

| Ingredients | % w/w |
|---|---|
| Entacapone layer/Portion | |
| Entacapone | 28.57 |
| Mannitol | 5.00 |
| Sodium starch glycolate | 2.86 |
| Corn Starch | 7.00 |
| Croscarmellose sodium | 3.43 |
| Povidone | 1.14 |
| Purified water | q.s. |

TABLE 3-continued

Pharmaceutical composition of the invention

| Ingredients | % w/w |
|---|---|
| Extragranular Ingredients | |
| Magnesium stearate | 0.57 |
| Levodopa and Carbidopa CR layer/Portion | |
| Levodopa | 28.57 |
| Carbidopa | 7.71 |
| Microcrystalline Cellulose | 6.86 |
| Povidone | 5.14 |
| Purified Water | q.s. |
| Extragranular Ingredients | |
| PVP | 2.57 |
| Magnesium Stearate | 0.57 |

Procedure:

Entacapone Layer/Portion:

Entacapone and mannitol were co-milled and sifted. Corn starch, croscarmellose sodium and sodium starch glycolate were co-sifted separately. The materials were placed in granulator and mixed. Povidone was dissolved in purified water and granulated with the mixed material. The granulated contents were dried. Magnesium stearate was sifted and mixed with the dried granules.

Levodopa and Carbidopa Layer/Portion:

Levodopa, Carbidopa and microcrystalline cellulose were co-sifted and mixed. Povidone was dissolved in Purified water and granulate with above mixed contents. The granulated contents were dried. Magnesium stearate was sifted with Poly Vinyl Pyrrolidone and mixed with the dried granules.

Compression

Both the entacapone layer/portion and Levodopa and Carbidopa layer/portion were compressed into bilayered tablets or into tablet in tablet with entacapone surrounding the levodopa-carbidopa inlay tablet.

TABLE 4

Dissolution data of composition prepared as per example II.

| Time (hrs) | % Drug released | |
|---|---|---|
| | Levodopa | Carbidopa |
| 0.5 | 43 | 43 |
| 1 | 58 | 58 |
| 2.5 | 88 | 89 |
| 4 | 98 | 98 |

| Time (min) | % Drug released (Entacapone) |
|---|---|
| 10 | 59 |
| 20 | 76 |
| 30 | 82 |
| 45 | 87 |

Table 4 provides the dissolution data of composition prepared as per formula given in table 3. For determination of drug release rate of entacapone, USP Type 2 Apparatus (rpm 50) was used wherein 900 ml of pH 5.5 phosphate buffer at 37° C.±0.5° C. was used as medium. Further, for determination of drug release rate of levodopa and carbidopa, USP Type 2 Apparatus (rpm 50) was used wherein 900 ml of 0.1 N HCl at 37° C.±0.5° C. was used as medium.

Example-III

TABLE 5

Pharmaceutical composition of the invention

| Ingredients | % w/w |
|---|---|
| Entacapone IR layer/Portion | |
| Entacapone | 36.36 |
| Mannitol | 21.27 |
| Povidone | 3.27 |
| Crospovidone | 4.36 |
| Magnesium stearate | 0.54 |
| Extragranular Ingredients | |
| Talc | 0.90 |
| Magnesium stearate | 0.54 |
| Levodopa and Carbidopa CR layer/Portion | |
| Levodopa | 18.18 |
| Carbidopa | 4.90 |
| Microcrystalline Cellulose | 4.36 |
| Povidone | 3.27 |
| Purified Water | q.s. |
| Extragranular Ingredients | |
| PVP | 0.16 |
| Magnesium Stearate | 0.03 |

Procedure:

Entacapone Layer/Portion:

Entacapone and mannitol were co-milled and sifted. Povidone, crospovidone and mannitol were co-sifted separately. The materials were mixed to form a bulk. Magnesium stearate was sifted and mixed with the above bulk. This was compacted and crushed. Magnesium stearate and talc were sifted separately and was mixed with the crushed material.

Levodopa and Carbidopa Layer/Portion:

Levodopa, Carbidopa and microcrystalline cellulose were co-sifted and mixed. Povidone was dissolved in Purified water and granulate with above mixed contents. The granulated contents were dried. Magnesium stearate was sifted with Poly Vinyl Pyrrolidone and mixed with the dried granules.

Compression

Both the entacapone layer/portion and Levodopa and Carbidopa layer/portion were compressed into bilayered tablets or into tablet in tablet with entacapone surrounding the levodopa-carbidopa inlay tablet.

Example-IV

TABLE 6

Pharmaceutical composition of the invention

| Ingredients | % w/w |
|---|---|
| Entacapone IR layer/Portion | |
| Entacapone | 27.39 |
| Mannitol | 21.27 |
| Povidone | 2.47 |
| Crospovidone | 3.29 |
| Magnesium stearate | 0.41 |

TABLE 6-continued

Pharmaceutical composition of the invention

| Ingredients | % w/w |
|---|---|
| Extragranular Ingredients | |
| Talc | 0.68 |
| Magnesium stearate | 0.41 |
| Levodopa and Carbidopa CR layer/Portion | |
| Levodopa | 27.39 |
| Carbidopa | 7.39 |
| Microcrystalline Cellulose | 6.58 |
| Povidone | 4.93 |
| Purified Water | q.s. |
| Extragranular Ingredients | |
| PVP | 2.46 |
| Magnesium Stearate | 0.54 |

Procedure:

Entacapone Layer/Portion:

Entacapone and mannitol were co-milled and sifted. Povidone, crospovidone and mannitol were co-sifted separately. The materials were mixed to form a bulk. Magnesium stearate was sifted and mixed with the above bulk. This was compacted and crushed. Magnesium stearate and talc were sifted separately and was mixed with the crushed material.

Levodopa and Carbidopa Layer/Portion:

Levodopa, Carbidopa and microcrystalline cellulose were co-sifted and mixed. Povidone was dissolved in Purified water and granulate with above mixed contents. The granulated contents were dried. Magnesium stearate was sifted with Poly Vinyl Pyrrolidone and mixed with the dried granules.

Compression

Both the entacapone layer/portion and Levodopa and Carbidopa layer/portion were compressed into bilayered tablets or into tablet in tablet with entacapone surrounding the levodopa-carbidopa inlay tablet.

Example V

TABLE 7

Pharmaceutical composition of the invention

| Ingredient | % w/w |
|---|---|
| Inner LC-ER core tablet | |
| Levodopa | 30.77 |
| Carbidopa | 8.31 |
| Hydroxy Propyl cellulose | 4.62 |
| Mannitol | 1.54 |
| Povidone K90 | 0.46 |
| Isopropyl alcohol | 0.00 |
| Dichloromethane | 0.00 |
| Magnesium stearate | 0.46 |
| Inner ER core tablet Weight | |
| External Entacapone IR granules | |
| Entacapone | 30.77 |
| Mannitol 25 | 5.38 |
| Sodium starch glycolate | 3.08 |
| Croscarmellose sodium | 3.69 |
| Corn starch | 7.54 |
| Povidone K30 | 1.23 |
| water | 0.00 |

TABLE 7-continued

Pharmaceutical composition of the invention

| Ingredient | % w/w |
|---|---|
| Sodium starch glycolate | 1.54 |
| Magnesium stearate | 0.62 |
| External Entacpone IR granules Weight | |
| Total Tablet weight | |

Procedure—Inner LC-ER Core Tablet

Levodopa, Carbidopa, Hydroxy Propyl cellulose & mannitol were co-sifted and mixed. Povidone K90 was dissolved in Isopropyl alcohol & Dichloromethane. The bulk of step 1 was granulated using step 2 solution and granules were dried. Magnesium stearate was added to prepared granules and lubricated granules were compressed to obtain core tablets.

External Entacapone IR Granules

Entacapone & mannitol were co-milled. Sodium starch glycolate, Croscarmellose sodium, Corn starch were co-sifted. Povidone K30 was dissolved in purified water and used to granulate the bulk of step 1. Granules were dried. Sodium starch glycolate was sifted through suitable mesh and added to above granules. Magnesium stearate was added to above mix.

Compression

Tablet in tablet of inner LC ER core tablets & external Entacpone IR granules were compressed using suitable compression machine

TABLE 8

| | LEVODOPA | | CARBIDOPA | |
|---|---|---|---|---|
| Time | Sinemet CR | Example-1 | Sinemet CR | Example-1 |
| 0 | 0 | 0 | 0 | 0 |
| 15 | 20 | 15 | 23 | 16 |
| 30 | 37 | 40 | 38 | 40 |
| 45 | 52 | 57 | 52 | 58 |
| 60 | 66 | 70 | 65 | 70 |
| 75 | 77 | 79 | 75 | 79 |
| 90 | 85 | 86 | 81 | 86 |
| 120 | 95 | 96 | 90 | 95 |
| 150 | 100 | 102 | 94 | 101 |
| 180 | 102 | 103 | 97 | 103 |

| For Entacapone | | |
|---|---|---|
| Time | Comtan | Example-V |
| 0 | 0 | 0 |
| 5 | 17 | 17 |
| 10 | 47 | 39 |
| 20 | 88 | 72 |
| 30 | 98 | 82 |
| 45 | 101 | 90 |

Table 8 provides the dissolution data of composition prepared as per formula given in table 7. For determination of drug release rate of entacapone, USP Type 2 Apparatus (rpm 50) was used wherein 900 ml of pH 5.5 phosphate buffer at 37° C.±0.5° C. was used as medium. Further, for determination of drug release rate of levodopa and carbidopa, USP Type 2 Apparatus (rpm 50) was used wherein 900 ml of 0.1 N HCl at 37° C.±0.5° C. was used as medium.

TABLE 9

Bio Data (Fasted State)

| PK Parameters | Ratio % (T/R) | 90% CI Lower Limit | 90% CI Upper Limit | Intra-CV (%) |
|---|---|---|---|---|
| For Entacapone - | | | | |
| Cmax | 105.42 | 75.03 | 148.11 | 56.28 |
| AUC t | 106.92 | 91.78 | 124.56 | 23.89 |
| AUV inf | 106.14 | 91.39 | 123.27 | 23.89 |
| For Carbidopa - | | | | |
| Cmax | 142.51 | 120.86 | 168.05 | 25.84 |
| AUC t | 142.04 | 120.91 | 166.86 | 25.23 |
| AUV inf | 141.54 | 120.78 | 165.87 | 24.84 |
| For Levodopa - | | | | |
| Cmax | 125.57 | 109.25 | 144.32 | 21.73 |
| AUC t | 112.57 | 97.92 | 129.41 | 21.76 |
| AUV inf | 112.58 | 97.88 | 129.49 | 21.84 |

Table 9 provides bio profile of LC ER and Entacapone IR combination tablets prepared as per example V under fasting condition versus Reference product Comtan® 200 mg+one tablet of Sinemet CR (Manufacturer: Merck; Levodopa 200+ Carbidopa 50 mg ER tablet. Study design include fasting two-way cross-over bioequivalence study in 15 normal, adult, human subjects under fed condition Example VI

TABLE 10

Pharmaceutical composition of the invention

| Ingredient | % w/w |
|---|---|
| Inner LC ER core tablet | |
| Levodopa | 30.30 |
| Carbidopa | 8.18 |
| Hydroxy Propyl cellulose | 4.55 |
| Mannitol | 1.97 |
| Methacrylic acid copolymer | 1.52 |
| Isopropyl alcohol | — |
| Dichloromethane | — |
| Magnesium stearate | 0.45 |
| External Entacpone IR granules | |
| Entacapone | 30.30 |
| Mannitol 25 | 5.30 |
| Sodium starch glycolate | 3.03 |
| Croscarmellose sodium | 3.64 |
| Corn starch | 7.42 |
| Povidone K30 | 1.21 |
| water | — |
| Sodium starch glycolate | 1.52 |
| Magnesium stearate | 0.61 |
| Total Tablet weight | |

Procedure:

Inner LC-ER Core Tablet

Levodopa, Carbidopa, Hydroxy Propyl cellulose & mannitol were co-sifted and mixed. Methacrylic acid copolymer was dissolved in Isopropyl alcohol & Dichloromethane. The bulk of step 1 was granulated using step 2 solution and granules were dried. Magnesium stearate was added to the bulk of step 3 and mixed. The bulk of step 4 was granulated using suitable punches to obtain core tablets.

External Entacapone IR Granules

Entacapone & mannitol were mixed and milled. Sodium starch glycolate, Croscarmellose sodium, Corn starch were co-sifted and mixed. Povidone K30 in was dissolved in purified water. The bulk of step 7 was granulated using step 8 solution and granules were dried. Sodium starch glycolate was added to the bulk of step 9 and mixed. Magnesium stearate was added to the bulk of step 10 and mixed.

Compression

Tablet in tablet dosage form was prepared using inner LC ER core tablets & external Entacpone IR granules using suitable compression machine.

We claim:

1. An oral single unit dose pharmaceutical composition in the form of a bilayered tablet comprising a) levodopa or salts thereof for extended release, b) carbidopa or salts thereof for extended release, and c) entacapone or salts thereof for immediate release, wherein a) and b) form a first layer of the tablet for extended release comprising levodopa at about 19.22 (% w/w), carbidopa at about 5.19 (% w/w), microcrystalline cellulose at 4.62 (% w/w) povidone at 3.46 (% w/w), and purified water (q.s.) based on the total weight of the tablet; and wherein c) forms a second layer of the tablet for immediate release comprising entacapone at about 30.77 (% w/w), mannitol 25 at 5.38 (% w/w), sodium starch glycolate at 4.62 (% w/w), croscarmellose sodium at 3.69 (% w/w), corn starch at 7.54 (% w/w), povidone K30 at 1.23 (% w/w), and magnesium stearate at 0.62 (% w/w), based on the total weight of the tablet.

2. The pharmaceutical composition of claim 1, wherein one tablet of the said composition exhibits no significant difference in rate and/or extent of absorption of entacapone as compared to 2-4 immediate release tablets comprising 200 mg of entacapone in the absence of levodopa and carbidopa; and no significant difference in rate and/or extent of absorption of levodopa and carbidopa as compared to one controlled release tablet comprising levodopa and carbidopa in the absence of entacapone at 3-4 hours after administration.

3. A method of treating Parkinson's disease in a mammal, comprising administering to a mammal in need thereof, a single unit oral dose pharmaceutical composition in the form of a bilayered tablet comprising a) levodopa or salts thereof for extended release, b) carbidopa or salts thereof for extended release, and c) entacapone or salts thereof for immediate release; wherein a) and b) form a first layer of the tablet for extended release comprising levodopa at about 19.22 (% w/w), carbidopa at about 5.19 (% w/w), microcrystalline cellulose at 4.62 (% w/w) and povidone at 3.46 (% w/w) and purified water (q.s.), based on the total weight of the tablet; and wherein c) forms a second layer of the tablet for immediate release comprising entacapone at about 30.77 (% w/w), mannitol 25 at 5.38 (% w/w), sodium starch glycolate at 4.62 (% w/w), croscarmellose sodium at 3.69 (% w/w), corn starch at 7.54 (% w/w), povidone K30 at 1.23 (% w/w), and magnesium stearate at 0.62 (% w/w), based on the total weight of the tablet.

4. The method of treatment of claim 3, wherein one tablet of the said composition exhibits no significant difference in rate and/or extent of absorption of entacapone as compared to 2-4 immediate release tablets comprising 200 mg of entacapone in the absence of levodopa and carbidopa; and no significant difference in rate and/or extent of absorption of levodopa and carbidopa as compared to one controlled release tablet comprising levodopa and carbidopa in the absence of entacapone at 3-4 hours after administration.

5. A method of reducing the "wearing off" phenomena in Parkinson's patients, comprising administering to patient in need thereof, a single unit oral dose pharmaceutical composition in the form of a bilayered tablet comprising
 a). levodopa or salts thereof for extended release,
 b). carbidopa or salts thereof for extended release and
 c). entacapone or salts thereof for immediate release;
wherein a) and b) form a first layer of the tablet for extended release comprising levodopa at about 19.22 (% w/w), carbidopa at about 5.19 (% w/w), microcrystalline cellulose at 4.62 (% w/w), povidone at 3.46 (% w/w), and purified water (q.s.), based on the weight of the tablet; and wherein c) forms a second layer of the tablet for immediate release comprising entacapone at about 30.77 (% w/w), mannitol 25 at 5.38 (% w/w), sodium starch glycolate at 4.62 (% w/w), croscarmellose sodium at 3.69 (% w/w), corn starch at 7.54 (% w/w), povidone K30 at 1.23 (% w/w), and magnesium stearate at 0.62 (% w/w), based on the weight of the tablet.

6. The method of reducing the "wearing off" phenomena of claim 5, wherein one tablet of the said composition exhibits no significant difference in rate and/or extent of absorption of entacapone as compared to 2-4 immediate release tablets comprising 200 mg of entacapone in the absence of levodopa and carbidopa; and no significant difference in rate and/or extent of absorption of levodopa and carbidopa as compared to one controlled release tablet comprising levodopa and carbidopa in the absence of entacapone at 3-4 hours after administration.

7. A process for preparing a single unit oral dose pharmaceutical composition in the form of a bilayered tablet comprising a) levodopa or salts thereof for extended release, and b) carbidopa or salts thereof for extended release, and c) entacapone or salts thereof for immediate release, wherein said process comprises: mixing a blend of a) and b) to form a first layer of the tablet, wherein a) and b) for extended release comprises levodopa at about 19.22 (% w/w), carbidopa at about 5.19 (% w/w), microcrystalline cellulose at 4.62 (% w/w), povidone at 3.46 (% w/w), and purified water (q.s.), based on the weight of the tablet; and forming a second layer of the tablet with c) for immediate release, wherein c) for immediate release comprises entacapone at about 30.77 (% w/w), mannitol 25 at 5.38 (% w/w), sodium starch glycolate at 4.62 (% w/w), croscarmellose sodium at 3.69 (% w/w), corn starch at 7.54 (% w/w), povidone K30 at 1.23 (% w/w), and magnesium stearate at 0.62 (% w/w), based on the weight of the tablet.

8. An oral single unit dose pharmaceutical composition in the form of a bilayered tablet adapted to facilitate the passage of levodopa across a blood brain barrier comprising a) levodopa or salts thereof for extended release, b) carbidopa or salts thereof for extended release, and c) entacapone or salts thereof for immediate release; wherein a) and b) form a first layer of the tablet for extended release comprising levodopa at about 19.22 (% w/w), carbidopa at about 5.19 (% w/w), microcrystalline cellulose at 4.62 (% w/w), povidone at 3.46 (% w/w), and purified water (q.s.), based on the total weight of the tablet; and wherein c) forms a second layer of the tablet for immediate release comprising entacapone at about 30.77 (% w/w), mannitol 25 at 5.38 (% w/w), sodium starch glycolate at 4.62 (% w/w), croscarmellose sodium at 3.69 (% w/w), corn starch at 7.54 (% w/w), povidone K30 at 1.23 (% w/w), and magnesium stearate at 0.62 (% w/w), based on the total weight of the tablet.

* * * * *